US00PP36425P2

(12) United States Plant Patent
Mousa

(10) Patent No.: US PP36,425 P2
(45) Date of Patent: Feb. 4, 2025

(54) ***HIBISCUS* PLANT NAMED 'Dohibcarbre'**

(50) Latin Name: *Hibiscus rosa-sinensis*
Varietal Denomination: Dohibcarbre

(71) Applicant: DUMMEN GROUP B.V., De Lier (NL)

(72) Inventor: Rami Mousa, De Lier (NL)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 18/662,997

(22) Filed: May 13, 2024

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
See application file for complete search history.

*Primary Examiner* — Susan McCormick Ewoldt
(74) *Attorney, Agent, or Firm* — C. Anne Whealy

(57) ABSTRACT

A new and distinct cultivar of *Hibiscus* plant named 'Dohibcarbre', characterized by its upright and mounding plant habit; moderately vigorous growth habit and moderate growth rate; freely branching habit; dense and bushy appearance; dark green-colored leaves; freely flowering habit; large double, reddish orange-colored flowers; and good container and garden performance and high temperature tolerance.

2 Drawing Sheets

Figure 1:
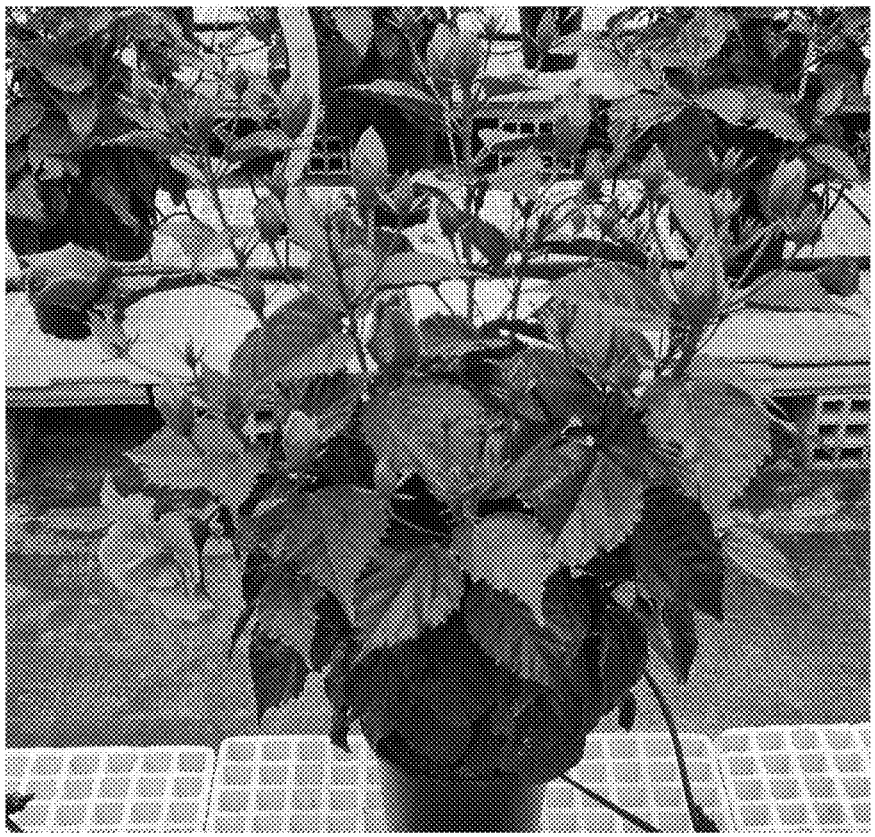

Botanical designation: *Hibiscus rosa-sinensis.*
Cultivar denomination: 'DOHIBCARBRE'.

STATEMENT REGARDING PRIOR DISCLOSURES BY INVENTOR and APPLICANT/ASSIGNEE

The Inventor and Applicant/Assignee assert that no sales, offers for sale or public distribution of the instant plant occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102 (b) (1) for disclosures and/or sales prior to the filing date but less than one year prior to the effective filing date.

BACKGROUND OF THE INVENTION

The present invention relates to a new and distinct cultivar of *Hibiscus* plant, botanically known as *Hibiscus rosa-sinensis,* and hereinafter referred to by the name 'Dohibcarbre'.

The new *Hibiscus* plant is a product of a planned breeding program conducted by the Inventor in De Lier, The Netherlands and Puerto Lumbreras, Murcia, Spain. The objective of the breeding program is to create new freely-branching *Hibiscus* plants with large attractive flowers and high temperature tolerance.

The new *Hibiscus* plant originated from a cross-pollination during the summer of 2019 in De Lier, The Netherlands of a proprietary selection of *Hibiscus rosa-sinensis* identified as code number HI-0027, not patented, as the female, or seed, parent with a proprietary selection of *Hibiscus rosa-sinensis* identified as code number HI-0017, not patented, as the male, or pollen, parent. The new *Hibiscus* plant was discovered and selected by the Inventor as a flowering plant within the progeny of the stated cross-pollination in a controlled greenhouse environment in Puerto Lumbreras, Murcia, Spain during the summer of 2020.

Asexual reproduction of the new *Hibiscus* plant by vegetative terminal cuttings in a controlled greenhouse environment in Puerto Lumbreras, Spain since the summer of 2020 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dohibcarbre'. These characteristics in combination distinguish 'Dohibcarbre' as a new and distinct *Hibiscus* plant:

1. Upright and mounding plant habit.
2. Moderately vigorous growth habit and moderate growth rate.
3. Freely branching habit; dense and bushy appearance.
4. Dark green-colored leaves.
5. Freely flowering habit.
6. Large double, reddish orange-colored flowers.
7. Good container and garden performance with high temperature tolerance.

Plants of the new *Hibiscus* can be compared to plants of the female parent selection. Plants of the new *Hibiscus* differ primarily from plants of the female parent selection in the following characteristics:

1. Plants of the new *Hibiscus* are not as vigorous as plants of the female parent selection.
2. Flowers of plants of the new *Hibiscus* are double-types whereas flowers of plants of the female parent selection are single-types.
3. Plants of the new *Hibiscus* are more high temperature tolerant than plants of the female parent selection.

Plants of the new *Hibiscus* can be compared to plants of the male parent selection. Plants of the new *Hibiscus* differ primarily from plants of the male parent selection in the following characteristics:

1. Plants of the new *Hibiscus* are more freely branching than plants of the male parent selection.
2. Plants of the new *Hibiscus* have larger leaves than plants of the male parent selection.
3. Plants of the new *Hibiscus* have smaller flowers than plants of the male parent selection.
4. Plants of the new *Hibiscus* are more high temperature tolerant than plants of the male parent selection.

Plants of the new *Hibiscus* can be compared to plants of the *Hibiscus rosa-sinensis* 'Adonicus Double Orange', not patented. In side-by-side comparisons, plants of the new *Hibiscus* differ from plants of 'Adonicus Double Orange' in the following characteristics:

1. Plants of the new *Hibiscus* are shorter than plants of 'Adonicus Double Orange'.
2. Plants of the new *Hibiscus* have shorter internodes than plants of 'Adonicus Double Orange'.
3. Plants of the new *Hibiscus* are more freely branching than plants of 'Adonicus Double Orange'.
4. Leaves of plants of the new *Hibiscus* are larger and stronger than leaves of plants of 'Adonicus Double Orange'.
5. Plants of the new *Hibiscus* are more freely flowering than plants of 'Adonicus Double Orange'.
6. Flowers of plants of the new *Hibiscus* are darker reddish orange in color than flowers of plants of 'Adonicus Double Orange'.
7. Plants of the new *Hibiscus* are more high temperature tolerant than plants of 'Adonicus Double Orange'.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet FIG. 1 is a side perspective view of a typical flowering plant of 'Dohibcarbre' grown in a container.

Figure 2:
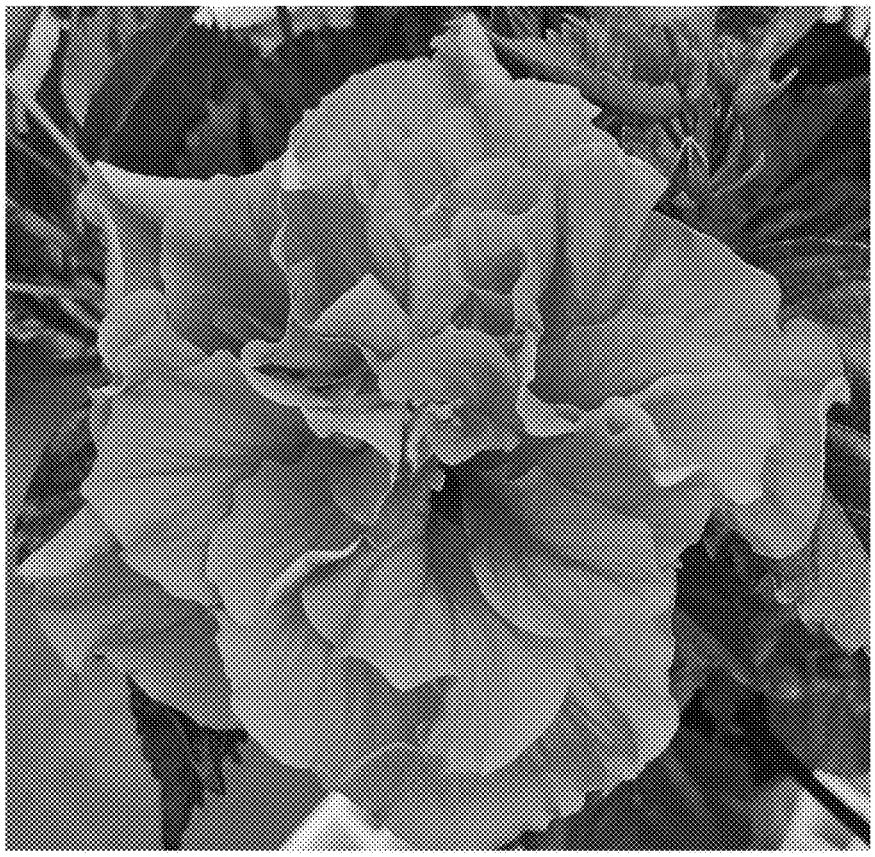

The photograph on the second sheet FIG. 2 is a close-up view of a typical flower of 'Dohibcarbre'.

DETAILED BOTANICAL DESCRIPTION

The aforementioned photographs and following observations, measurements and values describe plants grown during the summer in 15-cm containers in a glass-covered greenhouse in De Lier, The Netherlands and under cultural practices typical of commercial *Hibiscus* production. During the production of the plants, day temperatures ranged from 20° C. to 35° C., night temperatures ranged from 17° C. to 25° C. and light levels were at least 135 watt/$m^2$. Plants were pinched one time four weeks after planting and a second time twelve weeks after planting. Plants were 24 weeks old when the photographs and the description were taken. In the description, color references are made to The Royal Horticultural Society Colour Chart, Fifth Edition, except where general terms of ordinary dictionary significance are used.

Botanical classification: *Hibiscus rosa-sinensis* 'Dohibcarbre'.

Parentage:

*Female, or seed, parent*.—Proprietary selection of *Hibiscus rosa-sinensis* identified as code number HI-0027, not patented.

*Male or pollen parent*.—Proprietary selection of *Hibiscus rosa-sinensis* identified as code number HI-0017, not patented.

Propagation:

*Type*.—By vegetative terminal cuttings.

*Time to initiate roots, summer*.—About two to three weeks at temperatures about 25° C. to 40° C.

*Time to initiate roots, winter*.—About three to four weeks at temperatures about 18° to 22° C.

*Time to produce a rooted young plant, summer*.—About six weeks at temperatures about 25° C. to 40° C.

*Time to produce a rooted young plant, winter*.—About eight weeks at temperatures about 18° C. to 22° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright and mounding plant habit; moderately vigorous growth habit and moderate growth rate.

*Branching habit*.—Freely branching habit with usually about five primary branches each with about three secondary branches developing per plant; pinching enhances lateral branch development; dense and bushy appearance.

*Plant height, soil level to top of foliar plane*.—About 40 cm.

*Plant height, soil level to top of floral plane*.—About 45 cm.

*Plant diameter* (*area of spread*).—About 38 cm.

Lateral branch description:

*Length*.—About 30 cm.

*Diameter*.—About 7 mm.

*Internode length*.—About 5.5 cm.

*Strength*.—Strong.

*Texture and luster*.—Smooth, glabrous; semi-glossy.

*Color, developing*.—Close to 144A.

*Color, developed*.—Close to 148A.

Leaf description:

*Arrangement*.—Alternate, single.

*Length*.—About 14 cm.

*Width*.—About 9.5 cm.

*Shape*.—Ovate.

*Apex*.—Acute.

*Base*.—Obtuse.

*Margin*.—Crenate with shallow and divergent indentations.

*Texture and luster, upper and lower surfaces*.—Smooth, glabrous; glossy.

*Venation pattern*.—Pinnate; arcuate.

*Color*.—Developing leaves, upper surface: Close to 141B. Developing leaves, lower surface: Close to 143A. Fully expanded leaves, upper surface: Close to 139A; venation, close to 143A. Fully expanded leaves, lower surface: Close to 143B; venation, close to 143B.

*Petioles*.—Length: About 4.1 cm. Diameter: About 2 mm. Texture and luster, upper and lower surfaces: Smooth, glabrous; semi-glossy. Color, upper and lower surfaces: Close to 144A.

Flower description:

*Flower arrangement*.—Double-type flowers arranged singly at terminal leaf axils; uniform, continuous and freely flowering habit with numerous flowers developing per plant; flowers face mostly upright to outwardly and occasionally, nodding.

*Fragrance*.—None detected.

*Natural flowering season*.—Plants flower in the garden from late spring throughout the summer; in the greenhouse, plants can be flowered year-round; depending on temperature, plants begin flowering about 24 to 28 weeks after planting.

*Flower longevity*.—Good flower longevity; depending on temperature, flowers last for about five days; flowers not persistent.

*Flower diameter*.—About 12 cm.

*Flower length* (*height*).—About 4 cm.

*Flower buds*.—Length: About 3.5 cm. Diameter: About 2 cm to 3 cm. Shape: Conical. Texture and luster: Smooth, glabrous; satiny; matte. Color: Close to 144B.

*Petals*.—Arrangement: Five petals in a single whorl. Length: About 8 cm. Width: About 10 cm. Shape: Roughly spatulate. Apex: Rounded. Base: Rounded. Margin: Entire; slightly undulate. Texture and luster, upper surface: Smooth, glabrous; semi-glossy. Texture and luster, lower surface: Smooth, glabrous; matte. Color: When opening, upper and lower surfaces: Close to 33A. Fully opened, upper surface: Close to 34A; color becoming closer to 30A with subsequent development; venation, close to 41A. Fully opened, lower surface: Close to 33A; color becoming closer to 39B with subsequent development; venation, close to 32A.

*Petaloids*.—Arrangement: About five to seven, fused at the base. Arrangement: Five petals in a single whorl. Length: About 4.3 cm to 5.7 cm. Width: About 2.7 cm to 4.6 cm. Shape: Variable, roughly spatulate. Apex: Rounded. Base: Rounded. Margin: Entire; slightly undulate. Texture and luster, upper surface: Smooth, glabrous; semi-glossy. Texture and luster, lower surface: Smooth, glabrous; matte. Color: When opening, upper and lower surfaces: Close to 33A. Fully opened, upper surface: Close to 34A; color becoming closer to 30A with subsequent development; venation, close to 41A. Fully opened, lower surface: Close to 33A; color becoming closer to 39B with subsequent development; venation, close to 32A. Throat: Close to 34B; venation, close to 34B.

*Sepals*.—Appearance: Six to eight sepals in a single whorl forming a campanulate-shaped calyx. Length: About 2 cm. Width: About 2 cm. Shape: Lanceolate. Apex: Acute. Base: Cordate. Margin: Entire. Texture and luster, upper and lower surfaces: Smooth, glabrous; semi-glossy. Color: When opening, upper and lower surfaces: Close to 143A. Fully opened, upper and lower surfaces: Close to 143A.

*Involucral bracts*.—Quantity and arrangement: About six in a single whorl subtending the calyx and forming a star-shaped epicalyx. Length: About 1 cm to 1.5 cm. Diameter: About 2 mm to 5 mm. Shape: Lanceolate. Apex: Acute. Margin: Entire. Texture, upper and lower surfaces: Smooth, glabrous. Color, upper and lower surfaces: Close to 141A.

*Peduncles*.—Length: About 7 cm to 8 cm. Diameter: About 7 mm. Strength: Moderately strong. Aspect: Mostly upright. Texture and luster: Smooth, glabrous; semi-glossy. Color: Close to 143A.

*Reproductive organs*.—Androecium: Stamen number: About 25 to 30. Filament length: About 1 cm. Filament color: Close to 7A. Anther length: About 7 mm to 8 mm. Anther width: About 2 mm to 3 mm. Anther shape: Round. Anther color: Close to 15A. Amount of pollen: Moderate. Pollen color: Close to 9A.

*Gynoecium*.—Pistil length: About 7 cm to 8 cm. Staminal column texture: Smooth, waxy. Staminal column color: Close to 144A. Stigma appearance: Five rounded stigma pads. Stigma pad diameter: About 1 cm. Stigma pad color: Close to 51A. Ovary color: Close to 144A.

*Seeds*.—Quantity per fruit: Typically about two to eight develop. Length: About 1 cm to 2 cm. Diameter: About 8 mm to 10 mm. Texture: Smooth. Color: Close to 183A.

Temperature tolerance: Plants of the new *Hibiscus* have been observed to tolerate temperatures from about 10° C. to about 45° C.

Pathogen & pest resistance: Plants of the new *Hibiscus* not been observed to be resistant to pathogens and pests common to *Hibiscus* plants.

It is claimed:

1. A new and distinct *Hibiscus* plant named 'Dohibcarbre' as illustrated and described herein.

* * * * *